(12) United States Patent
Tanigawa et al.

(10) Patent No.: US 6,384,247 B2
(45) Date of Patent: May 7, 2002

(54) METHOD OF PRODUCING SESAMOL FORMIC ACID ESTER AND SESAMOL

(75) Inventors: Hiroto Tanigawa; Kenji Oka, both of Ohtake (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/881,063

(22) Filed: Jun. 15, 2001

(30) Foreign Application Priority Data

Jun. 19, 2000 (JP) ........................................ 2000-182755

(51) Int. Cl.[7] .............................................. C07D 317/44
(52) U.S. Cl. ........................................ 549/437; 549/438
(58) Field of Search .................................. 549/437, 438

(56) References Cited

U.S. PATENT DOCUMENTS

| 4,499,115 A | * | 2/1985 | Minh et al. | 426/546 |
| 4,876,277 A | * | 10/1989 | Burke et al. | 514/465 |
| 5,936,103 A | * | 8/1999 | Panseri et al. | 549/437 |
| 6,252,092 B1 | * | 6/2001 | Borzatta | 549/434 |

FOREIGN PATENT DOCUMENTS

SU 688492 9/1979

OTHER PUBLICATIONS

Synthesis, Mar., 1989, 167–172; The Bayer–Villiger Oxidation of Aromatic Aldehydes and Ketones with Hydrogen Peroxide Catalyzed.
J. Org. Chem. 1984, 49, 4740–4741; Acid–Catalyzed Oxidation of Benzaldehydes to Phenols by Hydrogen Peroxide.
Sekiyu Gakkaishi, 29, (5), 364–372 (1986); Synthesis of fine Chemicals by the Use of Oxidation.
Indian Journal of Chemistry, vol. 22B, No. 1983, p. 1150; Synthesis of 2,2–dimethyl–6, 7–methylenedioxybennzo (1,2–b) pyran.

* cited by examiner

Primary Examiner—Deborah C Lambkin
(74) Attorney, Agent, or Firm—Nixon & Vanderhye P.C.

(57) ABSTRACT

Heliotropin is oxidized with a percarboxylic acid in the presence of formic acid and an optionally added organic solvent, to thereby produce sesamol at high efficiency while suppressing by-production of heliotropic acid.

9 Claims, No Drawings

METHOD OF PRODUCING SESAMOL FORMIC ACID ESTER AND SESAMOL

BACKGROUND OF THE INVENTION

1. Field of the Invention

The present invention relates to a method of producing a sesamol formic acid ester (hereinafter referred to as sesamyl formate) with a low by-product yield of heliotropic acid, and to a method of producing sesamol by conducting hydrolysis or alcoholysis of the ester.

2. Background Art

Sesamol—3,4-(methylenedioxy)phenol—is a compound in the form of white crystals (melting point 65.5° C.) having a phenol odor, and serves as an important starting material for producing pharmaceuticals such as hypotensive agents. Sesamol also finds uses such as antioxidants, antibacterial agents, herbicides, and cosmetics.

Conventionally, several methods of producing sesamol from heliotropin as a starting material are known. For example, the following methods are disclosed:

(1) reacting heliotropin with hydrogen peroxide in methylene chloride serving as a solvent and in the presence of caustic soda and a selenium compound (*Synthesis*, 1989, March, 167);

(2) reacting heliotropin with peracetic acid or hydrogen peroxide in methylene chloride serving as a solvent (*J. Org. Chem.*, 1984, 49, 4741 and *Sekiyu-gakkai shi* 29, (5), 364 (1986));

(3) reacting heliotropin with chloroperbenzoic acid in methylene chloride serving as a solvent (*Ind. J. Chem.*, 1983, 22, 1150);

(4) reacting heliotropin with performic acid in chloroform serving as a solvent (USSR Patent No. 688492); and (5) reacting heliotropin with peracetic acid in ethyl acetate serving as a solvent (Japanese Patent Application Laid-Open (kokai) No. Heisei7-25868).

The aforementioned method (1), which employs a highly toxic selenium compound, is difficult to carry out on an industrial scale. Methods (2) to (4) are also difficult to carry out on an industrial scale, since these methods employ a halogen-containing solvent, whose use as been discouraged in recent years due to environmental impact.

Although the aforementioned method (5) is advantageous in that it can be carried out in ethyl acetate (i.e., a chlorine-free customary solvent), generation of a large amount of heliotropic acid, which is a by-product difficult to dissolve in most customary solvents including ethyl acetate, requires an alkali-extraction step, thereby making the production steps cumbersome.

Specifically, Japanese Patent Application Laid-Open (kokai) No. Heisei7-25868—related to method (5)—discloses a step of producing sesamyl formate by oxidizing heliotropin with peracetic acid in a specific organic solvent and in the absence of water; a step of producing sesamol by hydrolyzing the ester, without separation of the ester, in the presence of a base or water; and a step of obtaining (purifying) sesamol by separating the organic layer formed during the hydrolysis from the aqueous layer and subjecting the organic layer to distillation. Since this method produces a large amount of heliotropic acid as a by-product, the hydrolysis mixture is subjected to phase-separation so as to dissolve the by-product in the formed aqueous layer for removal thereof.

Increase in by-product yield of heliotropic acid reduces the yield of sesamol and generates solid deposits, to thereby render handling of the reaction mass difficult.

SUMMARY OF THE INVENTION

The present inventors have carried out extensive studies so as to solve the aforementioned problems, and have found that the by-product yield of heliotropic acid can be remarkably reduced by oxidizing heliotropin with peracetic acid in the presence of formic acid. The present invention has been accomplished on the basis of this finding.

Accordingly, an object of the present invention is to provide a method of producing sesamol with high efficiency.

In one aspect of the invention, there is provided a method of producing sesamyl formate, which comprises oxidizing heliotropin with a percarboxylic acid in the presence of formic acid and an optionally added organic solvent.

Preferably, the yield of by-produced heliotropic acid is 5 mol % or less.

Preferably, formic acid is added in an amount of 25–500 wt. % based on 100 wt. % of heliotropin.

Preferably, the percarboxylic acid has 1–7 carbon atoms.

Preferably, the organic solvent is a C1–C7 carboxylic acid; a C1–C6 alcohol ester of a C1–C7 carboxylic acid; or a mixture thereof.

In a second aspect of the invention, there is provided a method of producing sesamol, which comprises decomposing, by adding water and/or alcohol, sesamyl formate obtained through the aforementioned method of producing sesamyl formate.

Preferably, sesamyl formate is decomposed in the presence of a basic catalyst.

Preferably, the catalyst is removed after decomposition; a low-boiling-point substance is separated; and, successively, sesamol is collected through distillation.

Preferably, the catalyst is allowed to remain after decomposition; a low-boiling-point substance is separated; and, successively, sesamol is collected through distillation.

DETAILED DESCRIPTION OF PREFERRED EMBODIMENTS

The method of producing sesamol of the present invention comprises oxidizing heliotropin with a percarboxylic acid in the presence of formic acid, to thereby produce sesamyl formate, and hydrolyzing or alcoholyzing the thus-formed sesamyl formate, to thereby produce sesamol.

The method of the present invention will next be described in detail.

Heliotropin serving as a starting material can be obtained through isomerization of a source such as safrole (contained in camphor oil or ocotea oil) by heating with a caustic alkali, to thereby form isosafrole, and oxidizing the thus-formed isosafrole by use of ozone or a bichromate salt.

The method of the present invention, which produces sesamol from heliotropin serving as a staring material via sesamyl formate, is schematized by the following reaction scheme.

scheme

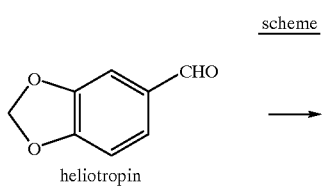

heliotropin

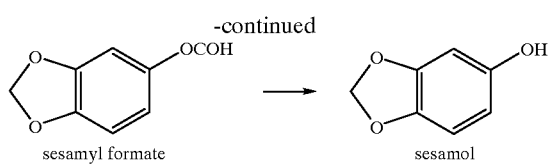

sesamyl formate → sesamol (a) In the first step (Baeyer-Villiger reaction), heliotropin is dissolved in formic acid per se or in a mixture of formic acid and a solvent, and a percarboxylic acid is added to the resultant mixture, to thereby form sesamyl formate.

The percarboxylic acid preferably has 1–7 carbon atoms, and specific examples thereof include performic acid, peracetic acid, perpropionic acid, perbutyric acid, and perbenzoic acid, with peracetic acid being particularly preferred.

Formic acid is used in an amount of 25–500 wt. %, preferably 50–200 wt. %, based on heliotropin. When the amount is less than 25 wt. %, heliotropic acid is generated as a by-product at an undesirable yield of greater than 5 mol %, whereas when the amount is in excess of 500 wt. %, a large amount of formic acid must be distilled off during a purification step, leading to a disadvantage with respect to energy consumption.

The percarboxylic acid is used in an amount by mol of 1–5 times that of heliotropin, preferably 1–2 times. When the amount of the percarboxylic acid is less than equimol, conversion cannot reach 100 mol % theoretically, whereas when the amount is in excess of 5 times, the amount of the remaining percarboxylic acid increases, leading to an economic disadvantage and requiring cumbersome post treatment.

If water is contained in the reaction system, sesamyl formate is hydrolyzed, to thereby form sesamol, and the formed sesamol is oxidized by percarboxylic acid such as peracetic acid. Thus, the absence of water is preferred. The water content of formic acid and percarboxylic acid is preferably minimized. Specifically, the employed formic acid preferably has a purity of 95 wt. % or higher (water content: 5 wt. % or lower), more preferably a purity of 98 wt. % or higher (water content: 2 wt. % or lower). The percarboxylic acid is preferably used in the form of a solution thereof in water-free ethyl acetate serving as a solvent.

A water-free percarboxylic acid solution; e.g., a solution of peracetic acid in ethyl acetate, can be obtained through, for example, air-oxidation of a solution of acetaldehyde in ethyl acetate.

As the aforementioned solvent to be used with formic acid, any solvent inert to peracid can be used so long as the solvent can dissolve the starting material and the products. Examples of the solvent include esters such as ethyl acetate and ethyl formate, and organic acids such as acetic acid and propionic acid. Of these, esters such as ethyl acetate are preferred.

If an alcohol such as methanol, ethanol, or propanol is employed as the solvent, sesamyl formate will undergo alcoholysis during reaction, and the thus-formed sesamol is oxidized by percarboxylic acid such as peracetic acid. Thus, alcohol is not preferably used as the solvent.

The solvent is used in an amount 300 wt. % or less based on heliotropin, preferably 100 wt. % or less. When the amount is in excess of 300 wt. %, a large amount of solvent must be distilled off during a purification step, leading to a disadvantage with respect to energy consumption.

The reaction temperature is not particularly limited. However, a temperature not higher than 100.5° C. (boiling point of formic acid) or not higher than the boiling temperature of a formic acid-solvent mixture is preferred. Specifically, when ethyl acetate (boiling point 77° C.) is employed as a solvent, reaction is carried out at 0–70° C., preferably 30–60° C. A reaction temperature of 0° C. or lower is appropriate because the rate of reaction is excessively low, whereas when the temperature is 70° C. or higher, the amount of required heat increases due to boiling the solvent, leading to a disadvantage with respect to energy consumption.

The reaction time, which varies depending on reaction conditions and the type and amount of the catalyst employed, is typically 2–10 hours.

No particular limitation is imposed on the pressure under which reaction is carried out, and the reaction may be carried out under atmospheric pressure, reduced pressure, or pressurized conditions. When reaction is carried out under pressure, the reaction temperature can be further elevated, to thereby shorten the reaction time and allow use of a solvent of low boiling point. When reaction is carried out under reduced pressure, a solvent of high boiling point can be used.

The reaction may also be carried out while vaporizing formic acid or a solvent; removing heat; or separating water from condensed liquid.

(b) In the second step (decomposition of sesamyl formate), the ester is undergoes hydrolysis and/or alcoholysis by adding water and/or alcohol, to thereby obtain sesamol. Examples of the alcohol include methanol, ethanol, and propanol.

After completion of the first step, formic acid and the solvent such as acetic acid or ethyl acetate may be distilled off or may remain as they are. However, these components are preferably distilled off. The formed sesamyl formate may be separated or may remain in the reaction mixture, so as to perform ester decomposition (the second step).

Water and/or alcohol are used in an amount by mol of 1–100 times that of sesamyl formate, preferably 2–10 times. When the amount of water and/or alcohol is less than equimol, conversion cannot reach 100% theoretically, whereas when the amount is in excess of 100 times by mol, a large amount of solvent must be distilled off during the second step or a purification step, leading to a disadvantage in terms of energy consumption.

Generally, in order to accelerate the reaction, a basic catalyst such as caustic soda may be added. No particular limitation is imposed on the basic catalyst, and examples thereof include caustic soda, caustic potash, acetate salts thereof, formate salts thereof, and basic ion-exchange resin of these, caustic soda is preferred in view of cost.

The amount of the basic catalyst varies depending on the species of catalyst. For example, caustic soda or a salt thereof is used in an amount of 0.01–5 wt. % based on sesamol formate, preferably 0.1–1 wt. %. When the amount of such a catalyst is less than 0.01 wt. %, a sufficient rate of reaction cannot be attained, whereas when the amount is in excess of 5 wt. %, costs for preparing and collecting the catalyst disadvantageously increase.

No particular limitation is imposed on the reaction temperature. Since the reaction is generally carried out while distilling off by-produced formic acid or sesamyl formate, the crude reaction mixture is maintained in a boiling state.

No particular limitation is imposed on the reaction pressure, and the reaction may be carried out under atmospheric pressure, reduced pressure, or pressurized conditions.

The reaction time, which varies depending on reaction conditions and the type and amount of the catalyst employed, is typically 1–10 hours.

After completion of decomposition of sesamyl formate, the catalyst is neutralized or separated in accordance with need. Subsequently, remaining low-boiling point substances such as water or alcohol; formic acid or sesamyl formate; and a solvent are removed through, for example, distillation, and a crude mixture containing sesamol is subjected to distillation or steam distillation, to thereby obtain sesamol having a purity of 99% or higher.

The thus-obtained sesamol may further be purified through recrystallization or distillation in accordance with needs.

EXAMPLES

The present invention will next be described by way of examples, which should not be construed as limiting the invention thereto.

Example 1

A flask equipped with a thermometer, a reflux condenser, and a stirrer was charged with heliotropin (1,000 g), formic acid (1,000 g; purity=98 wt. %; water content=2 wt. %), and ethyl acetate (1,000 g), and a solution (2,100 g) of peracetic acid (30 wt. %) in ethyl acetate was added dropwise to the mixture at 40° C. over three hours. After two hours of aging, disappearance of peracetic acid was confirmed. Analysis by means of gas chromatography revealed that the crude reaction mixture contained 14 wt. % sesamyl formate and 4 wt. % sesamol, and no heliotropic acid was detected in the mixture. The yield (representing the total of sesamyl formate and sesamol, hereinafter the same meaning applies) on the basis of heliotropin was 87 mol %. The aforementioned crude mixture was a homogeneous solution, with no sedimentation of solid matter.

From the above crude mixture, low-boiling-point substances such as formic acid, ethyl acetate, and acetic acid were distilled off by use of an evaporator, to thereby obtain 1,050 g of a distillation residue.

The distillation residue was transferred to a flask to which an Oldershaw column of 20 stages had been attached. Ethanol (800 g; boiling point=78.3° C,) and 10 wt. % aqueous caustic soda solution (20 g) were added thereto, and alcoholysis was carried out under boiling and while allowing by-produced ethyl formate (boiling point=54.3° C.) to evaporate. The reaction temperature was 82° C. upon start of the reaction and 96° C. upon completion of the reaction (after 4.5 hours). When the reaction was completed, formic acid and excess ethanol were removed almost completely. Subsequently, sesamol was subjected to distillation under reduced pressure (110° C.; column-top pressure=3 mmHg), to thereby obtain 730 g of sesamol (purity=99.2 wt. %; melting point=63–64° C.). The overall yield of sesamol from the starting material, heliotropin, was 79 mol %.

Example 2

A flask equipped with a thermometer, a reflux condenser, and a stirrer was charged with heliotropin (1,000 g) and formic acid (500 g; purity=98 wt. %; water content=2 wt. %), and a solution (2,000 g) of peracetic acid (30 wt. %) in ethyl acetate was added dropwise to the mixture at 40° C. over one hour. After four hours of aging, disappearance of peracetic acid was confirmed. Analysis by means of gas chromatography revealed that the crude reaction mixture contained 21 wt. % sesamyl formate and 7 wt. % sesamol, and no heliotropic acid was detected in the mixture. The reaction yield was 93 mol %. The aforementioned crude mixture was a homogeneous solution, with no sedimentation of solid matter.

From the above crude mixture, low-boiling-point substances such as formic acid, ethyl acetate, and acetic acid were distilled off by use of an evaporator, to thereby obtain 1,050 g of a distillation residue.

Subsequently, similar to the procedure described in Example 1, the distillation residue was subjected to alcoholysis and distillation, to thereby obtain 740 g of sesamol (purity=99.2%: melting point=63–64° C.). The overall yield of sesamol from the starting material, heliotropin, was 80 mol %.

Comparative Example 1

A flask equipped with a thermometer, a reflux condenser, and a stirrer was charged with heliotropin (500 g) and ethyl acetate (500 g), and a solution (1,030 g) of peracetic acid (30 wt. %) in ethyl acetate (acetic acid content=6 wt. %) was added dropwise to the mixture at 50° C. over three hours. After five hours of aging, disappearance of peracetic acid was confirmed. Analysis by means of gas chromatography revealed that the crude reaction mixture contained 22 wt. % sesamyl formate and 2 wt. % heliotropic acid. The reaction yield was 81 mol % and the by-product yield of heliotropic acid was 7 mol %. White solid matter was deposited on the wall of the flask, and NMR analysis revealed this white solid matter to be heliotropic acid. The by-product yield of heliotropic acid inclusive of that deposited on the wall was 15 mol %, proving that the yield of target product was low as compared with the cases of Example 1 and Example 2, and the process was found to be disadvantageous in terms of economy.

In addition, deposition of heliotropic acid made handling of the reaction mass difficult.

Comparative Example 2

A flask equipped with a thermometer, a reflux condenser, and a stirrer was charged with heliotropin (1,000 g), formic acid (1,500 g; purity=98 wt. %; water content=2 wt. %), and concentrated sulfuric acid (0.2 g), and 60 wt. % aqueous hydrogen peroxide solution (560 g) was added dropwise to the mixture at 50° C. over one hour. Subsequently, the resultant mixture was subjected to aging for one hour. Analysis by means of gas chromatography revealed that the crude reaction mixture contained 2.8 wt. % sesamyl formate, 4.7 wt. % sesamol, and 9.2 wt. % heliotropin, and no heliotropic acid was detected in the mixture. A tar-like substance was observed at the bottom of the reactor. The reaction yield on the basis of heliotropin was 23 mol %, and the selectivity was 33%.

According to the method of the present invention, sesamol can be produced in a simple and convenient process without producing heliotropic acid as a by-product.

What is claimed is:

1. A method of producing sesamyl formate, which comprises oxidizing heliotropin with a percarboxylic acid in the presence of formic acid and an optionally added organic solvent.

2. The method of producing sesamyl formate according to claim 1, wherein the heliotropic acid is by-produced at a yield of 5 mol % or less.

3. The method of producing sesamyl formate according to claim 1, wherein the formic acid is added in an amount of 25–500 wt. % based on 100 wt. % of heliotropin.

4. The method of producing sesamyl formate according to claim 1, wherein the percarboxylic acid has 1–7 carbon atoms.

5. The method of producing sesamyl formate according to claim 1, wherein the organic solvent is a C1–C7 carboxylic acid; a C1–C6 alcohol ester of a C1–C7 carboxylic acid; or a mixture thereof.

6. A method of producing sesamol, which comprises decomposing, by adding water and/or alcohol, sesamyl formate obtained through a method of producing sesamyl formate as recited in claim 1.

7. The method of producing sesamol according to claim 6, wherein the sesamyl formate is decomposed in the presence of a basic catalyst.

8. The method of producing sesamol according to claim 7, wherein the catalyst is removed after decomposition; a low-boiling-point substance is separated; and, successively, sesamol is collected through distillation.

9. The method of producing sesamol according to claim 7, wherein the catalyst is allowed to remain after decomposition; a low-boiling-point substance is separated; and, successively, sesamol is collected through distillation.

* * * * *